(12) United States Patent
Fujita et al.

(10) Patent No.: US 9,140,585 B2
(45) Date of Patent: Sep. 22, 2015

(54) GAS SENSOR

(75) Inventors: Yasuhiro Fujita, Kaizu (JP); Takayoshi Atsumi, Konan (JP)

(73) Assignee: NGK SPARK PLUG CO., LTD., Nagoya (JP)

( * ) Notice: Subject to any disclaimer, the term of this patent is extended or adjusted under 35 U.S.C. 154(b) by 1074 days.

(21) Appl. No.: 13/205,920

(22) Filed: Aug. 9, 2011

(65) Prior Publication Data

US 2012/0036929 A1 Feb. 16, 2012

(30) Foreign Application Priority Data

Aug. 10, 2010 (JP) ................................ 2010-179403

(51) Int. Cl.
*G01D 11/24* (2006.01)
*G01N 27/407* (2006.01)

(52) U.S. Cl.
CPC .......... *G01D 11/245* (2013.01); *G01N 27/4078* (2013.01)

(58) Field of Classification Search
CPC .......................... G01D 11/245; G01N 27/4078
USPC ........................ 73/23.31, 31.05, 431; 204/426
See application file for complete search history.

(56) References Cited

U.S. PATENT DOCUMENTS

| | | | |
|---|---|---|---|
| 6,303,013 B1 * | 10/2001 | Watanabe et al. | ............. 204/428 |
| 7,424,819 B2 | 9/2008 | Fujita et al. | |
| 2008/0314117 A1 * | 12/2008 | Sato et al. | .................... 73/23.32 |

FOREIGN PATENT DOCUMENTS

JP 2007-285769 A 11/2007

* cited by examiner

*Primary Examiner* — Daniel S Larkin
(74) *Attorney, Agent, or Firm* — Leason Ellis LLP

(57) ABSTRACT

A gas sensor suppresses the deterioration of gas tightness caused by failure of a sealing material. The gas sensor includes: a housing; a sensor element arranged inside the housing; a sealing material filling a gap between the sensor element and the housing; an insulation member arranged on a proximal end side of the sealing material; and an annular metal ring arranged on a proximal end side of the insulation member. The sealing material, the insulation member and the metal ring are fixed under pressure by caulking from a proximal end side to a distal. A proximal-end facing surface of an inner peripheral portion of the metal ring is spaced apart from the caulking portion in an opposing region where an inner end of the caulking portion and the metal ring face each other in an opposed manner.

9 Claims, 10 Drawing Sheets

GAS SENSOR

CROSS-REFERENCE TO RELATED PATENT APPLICATIONS

This application claims the benefit of Japanese Patent Application No. 2010-179403, filed Aug. 10, 2010, all of which are incorporated by reference herein.

FIELD OF THE INVENTION

The present invention relates to a gas sensor which includes a sensor element for detecting concentration of a gas to be detected.

BACKGROUND OF THE INVENTION

As a gas sensor for detecting concentration of oxygen or NOx in an exhaust gas discharged from an automobile or the like, there has been known a gas sensor including a sensor element which uses a solid electrolyte.

As shown in FIG. 10, this type of gas sensor is configured such that a flange portion 3a is formed on a bottomed cylindrical sensor element (oxygen sensor element in this example) 3 in the vicinity of the center of the sensor element 3, and the sensor element 3 is inserted into and held on the inside of a cylindrical housing (main body fitting) 200 (JP-A-2007-285769 (FIG. 11)). A stepped portion 200e is formed on an inner peripheral surface of the housing 200, and a cylindrical ceramic holder 5 is arranged on a proximal end side of the stepped portion 200e by way of a packing 12. By bringing the flange portion 3a of the sensor element 3 into contact with the ceramic holder 5 from a proximal end side by way of a packing (not shown in the drawing), the flange portion 3a is brought into contact with the stepped portion 200e in an indirect manner.

Further, in a gap defined between the sensor element 3 and the housing 200 in the radial direction on a proximal end side of the flange portion 3a, a cylindrical sealing material (talc powder) 6 and an insulation member (ceramic sleeve) 50 are arranged. A metal ring (flat washer) 60 is arranged on a proximal end side of the insulation member 50, a caulking portion 200a is formed by bending a proximal end portion of the housing 200 inward so that the insulation member 50 is pressed toward a distal end side and collapses the sealing material 6 by pressing whereby the whole sensor element 3 is sealed while being fixed by caulking.

Further, a cylindrical outer sleeve 400 is joined to the proximal end portion of the housing 200 so as to hold a lead line and a terminal mounted on the proximal end side of the sensor element 3 and to cover the proximal end portion of the sensor element 3. On the other hand, a distal end of the sensor element 3 is covered with a protector 7. By threadedly mounting a male threaded portion 200d of the housing 200 of the gas sensor manufactured in this manner in a threaded hole formed in an exhaust pipe or the like, the distal end of the sensor element 3 is exposed in the inside of the exhaust pipe whereby the sensor element 3 can detect a gas to be detected (exhaust gas).

SUMMARY OF THE INVENTION

However, with respect to the technique disclosed in JP-A-2007-285769, gas tightness between the sensor element 3 and the housing 200 is lowered when the gas sensor is subjected to thermal cycle thus giving rise to a drawback that a gas to be detected outside the sensor flows into the inside of the sensor (inside of the outer cylinder 400). It is thought that when the gas sensor is heated, the housing 200 made of metal expands larger than the sealing material 6 and the insulation member 50 both of which are made of ceramic so that the caulked portion 200a is elongated toward the proximal end side in the longitudinal direction (ex direction in FIG. 10) whereby the caulking is loosened thus making the sealing by the sealing material 6 insufficient.

Accordingly, it is an object of the present invention to provide a gas sensor which can suppress the deterioration of gas tightness obtained by a sealing material.

To overcome the above-mentioned drawback, according to one aspect of the present invention, there is provided a gas sensor which includes: a cylindrical housing which extends in the axial direction; a sensor element which has a distal end side thereof projected from a distal end of the housing and is inserted into and is arranged in the inside of the housing; a sealing material which is filled in a gap defined between the sensor element and the housing; a cylindrical insulation member which is arranged on a proximal end side of the sealing material so as to surround the sensor element and has at least an outer surface of the proximal end portion thereof spaced apart from an inner surface of the housing; and an annular metal ring which is arranged on a proximal end side of the insulation member and has an outer peripheral portion thereof projected outward in the radial direction from the proximal end portion of the insulation member, wherein the sealing material, the insulation member and the metal ring are fixed by caulking in a pressed state from a proximal end side to a distal end side by a caulking portion which is formed by bending a proximal end portion of the housing inward, and the caulking portion is brought into close contact with the whole proximal-end facing surface of the outer peripheral portion of the metal ring, and at an inner peripheral portion of the metal ring formed inside the outer peripheral portion, at least a radially inner end portion of a proximal-end facing surface of the metal ring in an opposing region where the caulking portion and the metal ring face each other in an opposed manner in the axial direction is spaced apart from the caulking portion.

Due to such a constitution, when a stress which presses the outer peripheral portion of the metal ring downward (toward a distal end) is applied to the whole metal ring by caulking and the gas sensor is heated so that the caulking portion is elongated, the metal ring springs back in the direction opposite to the direction that the stress is applied. Due to this spring-back, a distal-end facing surface (distal end) side of the metal ring presses the insulation member downward toward a distal end and hence, loosening of caulking can be prevented whereby the deterioration of gas tightness obtained by the sealing material can be suppressed.

To be more specific, since the outer peripheral portion of the metal ring projects outward in the radial direction from the proximal end portion of the insulation member, a center axis of the metal ring is offset outward in the radial direction from a center axis of the insulation member in the radial direction. Accordingly, the center axis of the metal ring is positioned more outside in the radial direction than a fulcrum where a caulking load is supported and hence, in terms of moment, on a proximal-end facing surface of the metal ring, a major portion of caulking load is applied to an outer side of the proximal-end facing surface of the metal ring in the radial direction. Accordingly, the above-mentioned stress is generated thus bringing about a spring effect.

Further, the caulking portion is brought into close contact with the whole proximal-end facing surface of the outer peripheral portion of the metal ring and hence, a caulking load is surely applied to the outer peripheral portion whereby the above-mentioned stress is further increased.

Still further, at the inner peripheral portion of the metal ring, at least the radially inner end portion of the proximal-end facing surface of the metal ring in the opposing region where the caulking portion and the metal ring face each other in an opposed manner in the axial direction is spaced apart from the caulking portion and hence, the caulking load is hardly applied to the inner peripheral portion side of the metal ring and a major portion of the caulking load is applied to the outer peripheral portion side of the metal ring thus surely bringing about the above-mentioned spring-back effect.

Due to the above-mentioned constitution, the loosening of caulking can be prevented and hence, the deterioration of gas tightness obtained by the sealing material can be suppressed.

Here, "the proximal-end facing surface of the metal ring in the opposing region where the caulking portion and the metal ring face each other in an opposed manner in the axial direction in the inner peripheral portion of the metal ring" indicates the whole proximal-end facing surface of the inner peripheral portion of the metal ring when an inner end of the caulking portion is arranged more inside than the metal ring in the radial direction, for example. On the other hand, "the proximal-end facing surface of the metal ring in the opposing region where the caulking portion and the metal ring face each other in an opposed manner in the axial direction in the inner peripheral portion of the metal ring" indicates a portion of the proximal-end facing surface of the inner peripheral portion of the metal ring which is arranged outside a position where the proximal-end facing surface faces an inner end of the caulking portion in an opposed manner in the radial direction when the inner end of the caulking portion is arranged more outside than the metal ring in the radial direction, for example.

According to another aspect of the present invention, there is provided a gas sensor which includes: a cylindrical housing which extends in the axial direction; a sensor element which has a distal end side thereof projected from a distal end of the housing and is inserted into and is arranged in the inside of the housing; a sealing material which is filled in a gap defined between the sensor element and the housing; a cylindrical insulation member which is arranged on a proximal end side of the sealing material so as to surround the sensor element and has at least an outer surface of the proximal end portion thereof spaced apart from an inner surface of the housing; and an annular metal ring which is arranged on a proximal end side of the insulation member and has an outer peripheral portion thereof projected outward in the radial direction from the proximal end portion of the insulation member, wherein the sealing material, the insulation member and the metal ring are fixed by caulking in a pressed state from a proximal end side to a distal end side by a caulking portion which is formed by bending a proximal end portion of the housing inward, and a distal-end facing surface of the outer peripheral portion of the metal ring is positioned on a more distal-end side than a proximal-end facing surface of the proximal end portion of the insulation member.

Due to such a constitution, when a stress which presses the outer peripheral portion of the metal ring downward (toward a distal end) is applied to the whole metal ring by caulking and the gas sensor is heated so that the caulking portion is elongated, the metal ring springs back in the direction opposite to the direction that the stress is applied. Due to this spring-back, a distal-end facing surface (distal end) side of the metal ring presses the insulation member downward toward a distal end and hence, the loosening of caulking can be prevented whereby the deterioration of gas tightness obtained by the sealing material can be suppressed.

To be more specific, by applying a sufficient caulking load to an extent that the outer peripheral portion of the metal ring is positioned on a more distal end side than the proximal-end facing surface of the proximal end portion of the insulation member, the above-mentioned spring-back effect can be increased and hence, the loosening of caulking can be prevented whereby the deterioration of gas tightness obtained by the sealing material can be suppressed.

Here, "a distal-end facing surface of the outer peripheral portion of the metal ring is positioned on a more distal-end side than a proximal-end facing surface of the proximal end portion of the insulation member" indicates that the metal ring forcibly enters a gap defined between the insulation member and the housing.

Further, in the above-mentioned gas sensor, it is preferable that the caulking portion is brought into close contact with the whole proximal-end facing surface of the outer peripheral portion of the metal ring, and at the inner peripheral portion of the metal ring formed inside the outer peripheral portion, at least a radially inner end portion of the proximal-end facing surface of the metal ring where the caulking portion and the metal ring face each other in an opposed manner in the axial direction is spaced apart from the caulking portion.

Due to such a constitution, a caulking load is hardly applied to the inner peripheral portion of the caulking portion, and a major portion of the caulking load is applied to the outer peripheral portion side of the metal ring thus surely bringing about the above-mentioned spring back effect.

Further, in the gas sensor of the present invention, an inner end of the caulking portion may be positioned more outside in the radial direction than the inner surface of the metal ring.

Due to such a constitution, the position at which a caulking load is applied to the metal ring is arranged further closer to an outer peripheral side than an inner peripheral side of the metal ring. Accordingly, a stress which presses the outer peripheral side of the metal ring downward (toward a distal end) can be easily applied and hence, the above-mentioned spring back effect can be easily acquired correspondingly.

Further, in the gas sensor of the present invention, it is preferable that a contact portion between the caulking portion and the metal ring is positioned more inside in the radial direction than an outer surface of the insulation member. Although it is preferable that a caulking load is applied to the outer peripheral side of the metal ring, when a position where the caulking load is applied is excessively close to the outer peripheral side of the metal ring, only the outer peripheral portion of the metal ring is deformed thus giving rise to a possibility that the spring back effect is decreased. To the contrary, when the contact portion between the caulking portion and the metal ring is positioned more inside in the radial direction than the outer surface of the insulation member, it is possible to acquire the sufficient spring back effect while applying a caulking load to the outer peripheral side of the metal ring.

Further, in the gas sensor of the present invention, the inner surface of the metal ring may be positioned more outside in the radial direction than the inner surface of the insulation member.

Along with pressing the outer peripheral side of the metal ring downward with a load generated by caulking, the inner peripheral side of the metal ring is pressed upward (toward a distal end side). Here, due to such a constitution, a possibility that the inner surface of the metal ring is caught by an outer surface of the sensor element is decreased and hence, caulking can be surely performed.

Further, in the gas sensor of the present invention, a distal-end facing surface of the metal ring may be brought into face contact with the insulation member. Due to such a constitution, it is possible to secure an area where the distal-end facing surface of the metal ring is brought into contact with a proximal-end facing surface of the insulation member and hence, a spring force generated by the above-mentioned spring back can be surely applied to these members.

As one of means for bringing the distal-end facing surface of the metal ring into face contact with the insulation member, it is preferable that a cross section of the metal ring cut along a plane extending in the axial direction has a rectangular shape.

Due to such a constitution, since the distal-end facing surface of the metal ring is a planar surface, an area where the distal-end facing surface of the metal ring is brought into contact with the proximal-end facing surface of the proximal end portion of the insulation member is increased whereby a spring force generated by the above-mentioned spring back can be surely applied to these members.

Further, the proximal-end facing surface of the metal ring is also a planar surface and hence, an area where the metal ring is brought into contact with the caulking portion is also increased whereby a spring force generated by the spring back can be further surely applied to these members.

Further, in the gas sensor of the present invention, an outer surface of the insulation member may be formed into a straight shape. When a flange portion is formed on the insulation member, there exists a possibility that cracks occur in the flange portion due to a load of the caulking portion. However, by forming the outer surface of the insulation member into a straight shape, no cracks occur in the insulation member.

According to the present invention, it is possible to acquire a gas sensor which suppresses the deterioration of gas tightness obtained by a sealing material.

BRIEF DESCRIPTION OF THE DRAWINGS

These and other features and advantages of the present invention will become more readily appreciated when considered in connection with the following detailed description and appended drawings, wherein like designations denote like elements in the various views, and wherein.

DETAILED DESCRIPTION OF THE INVENTION

Description of the Preferred Embodiments

Hereinafter, embodiments of the present invention are explained.

Figure 1:
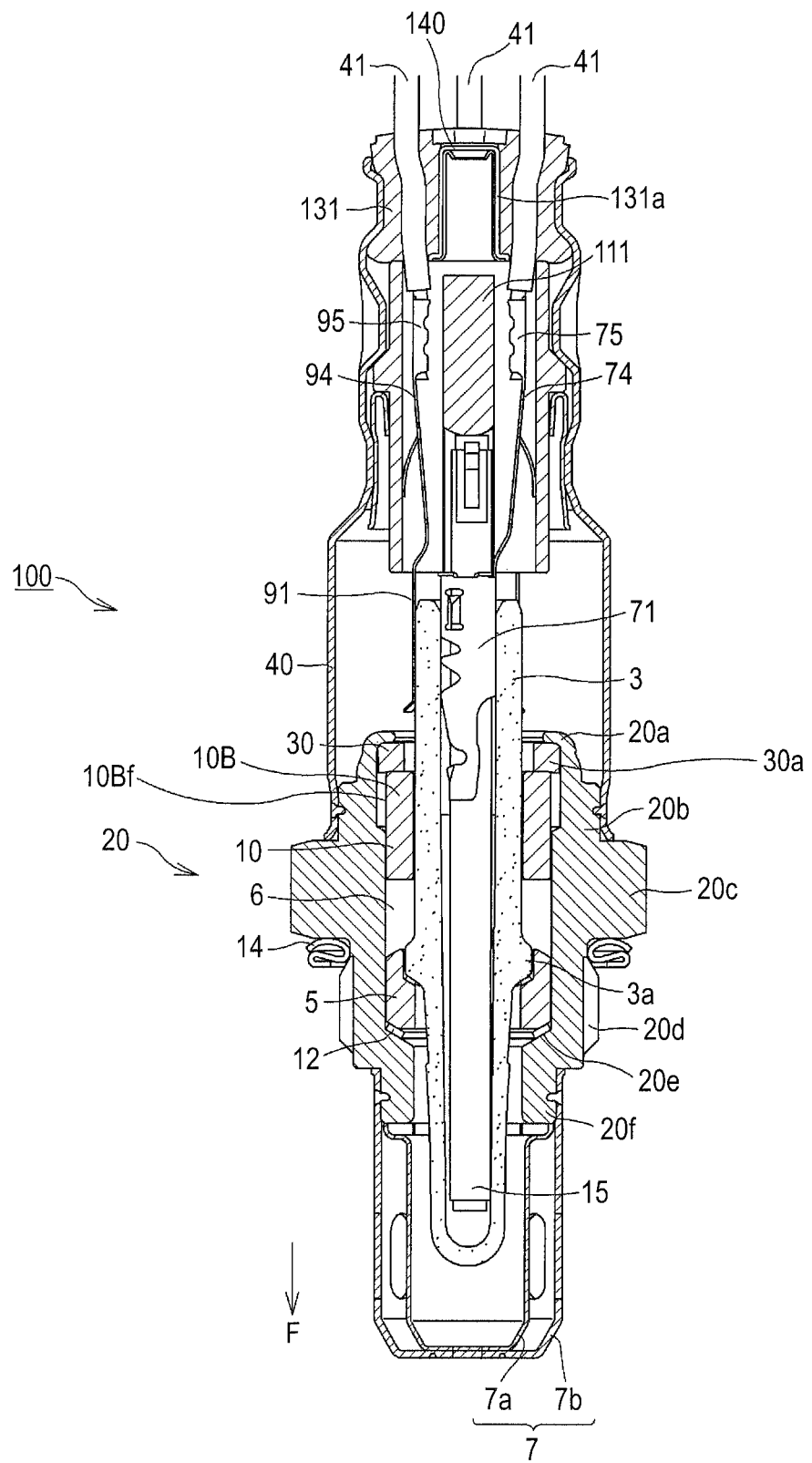
FIG. 1 is a cross-sectional view of a gas sensor according to a first embodiment of the present invention taken along a plane extending in the axial direction of the gas sensor.

FIG. 1 shows the cross-sectional structure of a gas sensor 100 according to a first embodiment of the present invention by cutting the gas sensor 100 along a plane extending in the axial direction (in the direction toward a proximal end from a distal end). In this embodiment, the gas sensor 100 is an oxygen sensor which is inserted into an exhaust pipe of an automobile and has a distal end (a side indicated by an arrow F in FIG. 1) thereof exposed in an exhaust gas thus detecting oxygen concentration in the exhaust gas. A sensor element 3 is a known oxygen sensor element which constitutes an oxygen concentration cell in which a pair of electrodes is stacked on a solid electrolytic body having oxygen ion conductivity and outputs a detection value corresponding to an oxygen quantity.

Here, a lower side of the gas sensor 100 in FIG. 1 (a side indicated by an arrow F) forms a distal end side of the gas sensor 100, and an upper side of the gas sensor 100 in FIG. 1 forms a proximal end side of the gas sensor 100.

The gas sensor 100 is an assembly where the sensor element 3 is assembled in a housing (main fitting) 20. The sensor element 3 is constituted of a solid electrolytic body having a cylindrical shape whose diameter is narrowed toward a distal end thereof in a tapered shape, and an inner electrode and an outer electrode (not shown in the drawing) which are formed on an inner peripheral surface and an outer peripheral surface of the solid electrolytic body respectively. A reference gas atmosphere is created in an inner space of the sensor element 3, and the gas detection is performed in such a manner that a gas to be detected is brought into contact with an outer surface of the sensor element 3. A rod-like heater 15 is inserted into the inner space of the sensor element 3.

A flange portion 3a which projects outward in the radial direction is formed on a portion of the sensor element 3 in the vicinity of the center of the sensor element 3. On the other hand, a stepped portion 20e which narrows a diameter thereof inward is formed on an inner peripheral surface of the housing 20 at a position close to a distal end of the housing 20, and a cylindrical ceramic holder 5 is arranged on a proximal end side of the stepped portion 20e by way of a packing 12. By inserting the sensor element 3 into the inside of the housing 20 and the ceramic holder 5 and by bringing the flange portion 3a of the sensor element 3 into contact with the ceramic holder 5 from a proximal end side by way of a packing (not shown in the drawing), the flange portion 3a of the sensor element 3 is brought into contact with the stepped portion 20e from the proximal end side in an indirect manner.

Further, a cylindrical sealing material (talc powder) 6 is filled in a gap which is defined between the sensor element 3 and the housing 20 in the radial direction on a proximal end side of the flange portion 3a, and a cylindrical insulation member (ceramic sleeve) 10 is arranged on a proximal end side of the sealing material 6. A metal ring (stainless steel-made flat washer) 30 is arranged on a proximal end side of the insulation member 10, and a caulking portion 20a is formed by bending a proximal end portion of the housing 20 inward so that the insulation member 10 is pressed toward a distal end side and collapses the sealing material 6 by pressing whereby the insulation member 10 and the sealing material 6 are fixed by caulking and also a gap defined between the sensor element 3 and the housing 20 is sealed. Here, there exists a possibility that cracks or the like occur when a proximal end of the insulation member 10 is directly caulked and hence, the caulking is performed by way of the metal ring 30.

Here, a diameter of the inner surface of the housing 20 is enlarged in the vicinity of the proximal end of the insulation member 10 so that at least an outer surface 10Bf of a proximal end portion 10B of the insulation member 10 is spaced apart from the inner surface of the housing 20. An outer diameter of the metal ring 30 is set larger than an outer diameter of the insulation member 10 so that, as described later, an outer peripheral portion 30a of the metal ring 30 projects outward in the radial direction from the outer surface 10Bf of the insulation member 10. The specification of the outer peripheral portion 30a of the metal ring 30 is described later.

Further, a cylindrical outer sleeve 40 is joined to a proximal end of the housing 20 for holding lead lines 41 and terminal fittings 71, 91 which are arranged on a proximal end side of the sensor element 3 and for covering the proximal end portion of the sensor element 3. To be more specific, a cylindrical separator 111 having an insulation property is fixed to a proximal-end-side inner surface of the outer sleeve 40 by caulking, and proximal portions 74, 94 of the terminal fittings 71, 91 are respectively inserted into and fixed to two through holes formed in the separator 111. Connection end portions 75, 95 are formed on proximal ends of the respective proximal portions 74, 94 respectively, and the lead lines 41, 41 are connected to the connection end portions 75, 95 respectively by caulking.

A cylindrical grommet 131 is fixed to an inner side of the outer sleeve 40 on a proximal end side of the separator 111 by caulking, and the lead lines 41, 41 are respectively pulled out to the outside from four through holes (only two through holes are shown in FIG. 1) formed in the grommet 131. When the outer sleeve 40 is arranged to cover the proximal end of the housing 20 in a state where the terminal fittings 71, 91 project toward a distal end side of the outer sleeve in this manner, the cylindrical terminal fitting 71 is fitted in a sleeve of the sensor element 3 and is electrically connected with a lead of a reference electrode on the inner surface of the sensor element 3. The terminal fitting 91 is fitted on an outer peripheral surface of the sensor element 3 and is electrically connected with a lead of a detection electrode formed on the outer surface of the sensor element 3. Further, a distal end of the outer sleeve 40 is fitted on the proximal end portion 20b of the housing 20, and the outer sleeve 40 is fixed to the housing 20 by welding both the outer sleeve 40 and the housing 20.

A through hole 131a is formed in the center of the grommet 131, and the through hole 131a is communicated with an inner space of the sensor element 3. Further, a water-repellent ventilation filter 140 is interposed in the center hole formed in the grommet 131 and hence, a reference gas (atmospheric air) can be introduced into the inner space of the sensor element 3 while preventing outside water from passing through the ventilation filter 140.

On the other hand, a cylindrical protector 7 is fitted on the distal end portion 20f of the housing 20, and the distal end of the sensor element 3 projecting from the housing 20 is covered with the protector 7. The protector 7 is formed by mounting a bottomed cylindrical outer protector 7b and a bottomed cylindrical inner protector 7a having the duplicate structure to the housing by the welding or the like, wherein the outer and inner protectors 7a, 7b have a plurality of hole portions (not shown in the drawing) and are made of metal (for example, stainless steel) respectively.

Here, a polygonal flange portion 20c which projects outward in the radial direction and is engageable with a hexagonal wrench or the like is formed on a portion of the housing 20 near the center of the housing 20, and a male threaded portion 20d is formed on an outer surface of the housing 20 between the flange portion 20c and the distal end portion 20f. On a stepped portion between a distal end surface of the flange portion 20c and a proximal end of the male threaded portion 20d, a gasket 14 which prevents the leaking of a gas when the gas sensor is mounted on an exhaust pipe is fitted.

By engaging the male threaded portion 20d of the housing 20 with a threaded hole formed in the exhaust pipe or the like, the distal end of the sensor element 3 is exposed in the inside of the exhaust pipe so that a gas to be detected (exhaust gas) can be detected.

Figure 2:
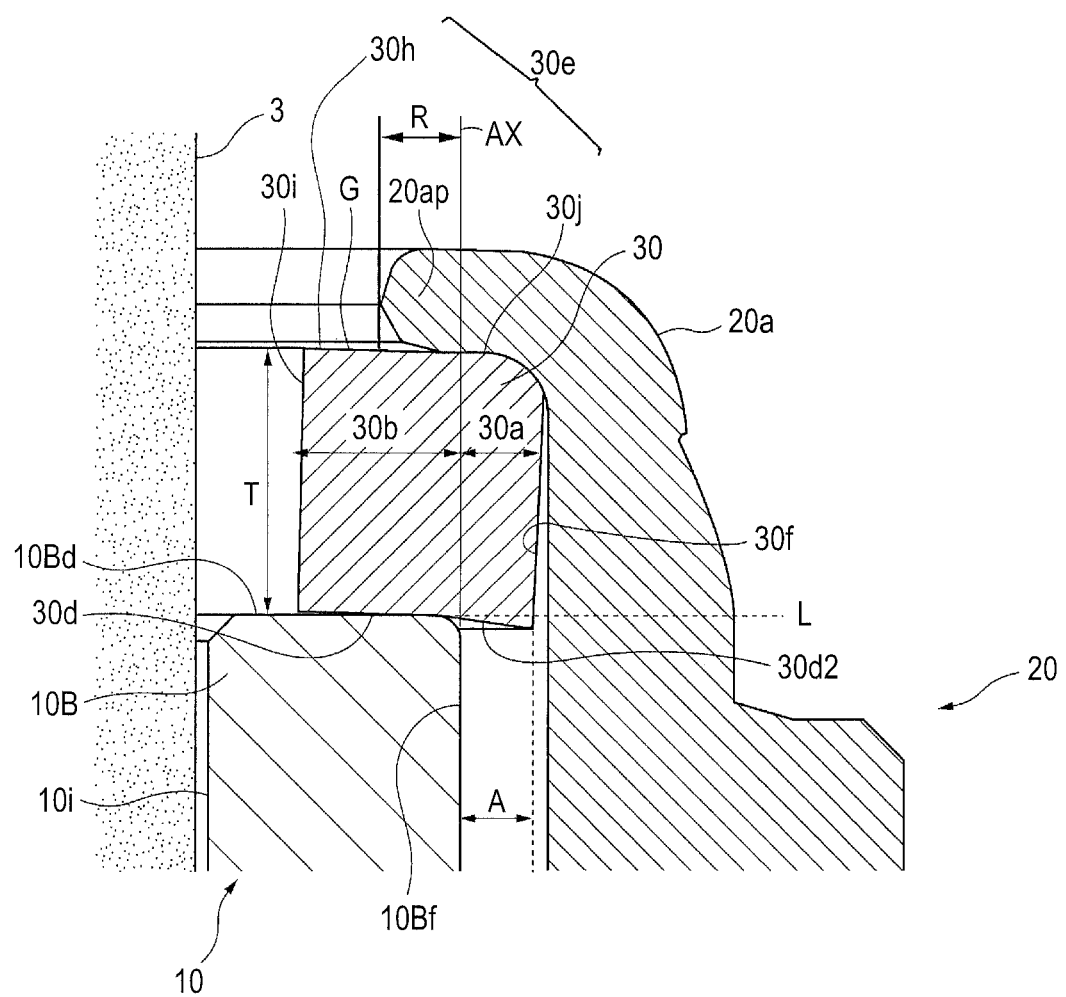
FIG. 2 is a partially enlarged view of FIG. 1.

Next, the positional relationship among the metal ring 30, the insulation member 10 and the housing 20 according to the first embodiment is explained in conjunction with FIG. 2.

An outer diameter of the metal ring 30 is set larger than an outer diameter of the insulation member 10 so that the outer peripheral portion 30a of the metal ring 30 projects outward in the radial direction from the outer surface 10Bf of the proximal end portion 10B of the insulation member 10. Here, the outer peripheral portion 30a of the metal ring 30 is a portion of the metal ring 30 which is positioned more outside in the radial direction than an imaginary line AX which extends in the axial direction from the outer surface 10Bf of the proximal end portion 10B of the insulation member 10. A portion of the metal ring 30 which is positioned more inside in the radial direction than the outer peripheral portion 30a is referred to as "inner peripheral portion 30b".

Figure 8:
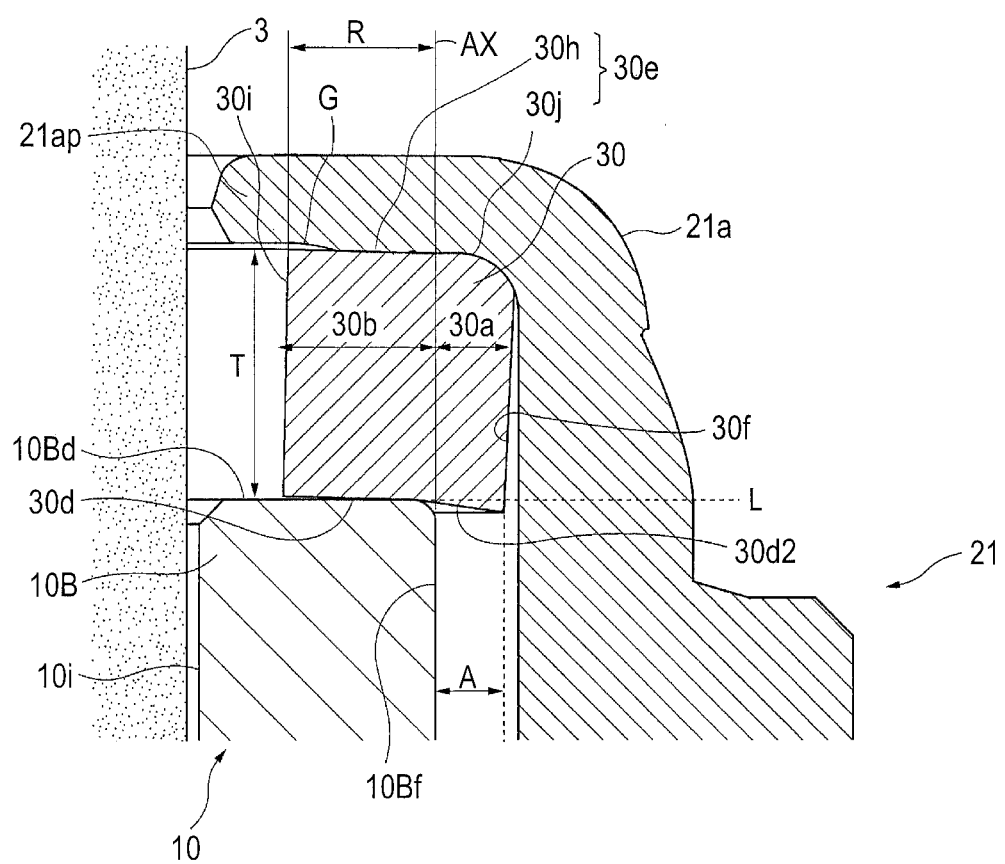
FIG. 8 is a cross-sectional view of the gas sensor according to the first embodiment of the present invention when an inner end of a caulking portion is arranged more inside in the radial direction than an inner surface of the metal ring.

The caulking portion 20a is brought into close contact with a whole proximal-end facing surface 30j of the outer peripheral portion 30a out of a proximal-end facing surface 30e of the metal ring 30. Further, an inner end 20ap of the caulking portion 20a is partially spaced apart from a proximal-end facing surface 30h of the inner peripheral portion 30b out of the proximal-end facing surface 30e of the metal ring 30 (a radially inner end portion of the proximal-end facing surface 30h). Here, in the inner peripheral portion 30b of the metal ring 30, a portion where the caulking portion 20a and the metal ring 30 face each other in an opposed manner in the axial direction (in the vertical direction in FIG. 2) is indicated as a facing region R. In the facing region R, it is not always necessary to bring the caulking portion 20a and the metal ring 30 into contact with each other in the axial direction, and the caulking portion 20a and the metal ring 30 may be arranged close to each other. For example, in, this embodiment, the inner end 20ap of the caulking portion 20a is positioned more outside in the radial direction than an inner surface 30i of the metal ring 30, and the inner end 20ap is spaced apart from the metal ring 30 in the axial direction. Further, as shown in FIG. 8, when an inner end 21ap of the caulking portion 21 is arranged more inside in the radial direction than the inner surface 30i of the metal ring 30, the facing region R indicates the whole inner peripheral portion 30b and hence, it is necessary to hold a caulking portion 21a in a non-contact state with the metal ring 30 at least on an inner end of the metal ring 30.

Further, in this embodiment, the inner surface 30i of the metal ring 30 is positioned more outside in the radial direction than an inner surface 10i of the insulation member 10. However, it is not a requisite to position the inner surface 30i more outside in the radial direction than the inner surface 10i, and the inner surface 30i may be made coplanar with the inner surface 10i. Here, in view of the relationship which allows the insertion of the sensor element 3, there is no case where the inner surface 30i is positioned more inside in the radial direction than the inner surface 10i.

Figure 3A:
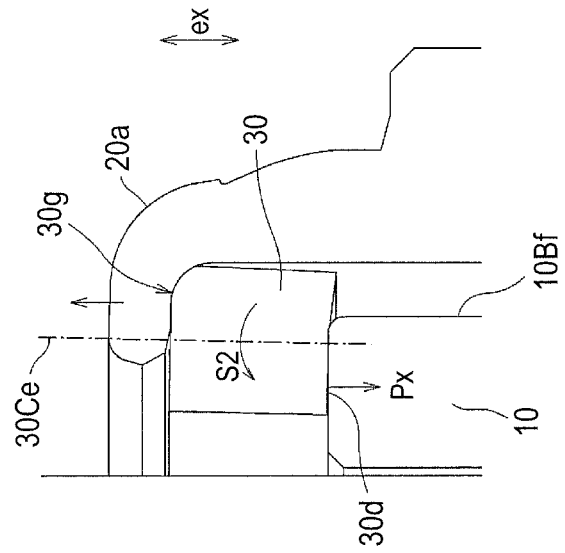
FIG. 3A and FIG. 3B are views showing a stress which is generated in caulking a metal ring and the manner of operation of a spring back corresponding to the stress.

As described above, the outer peripheral portion 30a of the metal ring 30 projects outward in the radial direction from the outer surface 10Bf of the proximal end portion 10B of the insulation member 10 and hence, as shown in FIG. 3A, center axis 30Ce of the metal ring 30 is offset outward in the radial direction from a center axis 10Ce of the insulation member 10 in the radial direction. That is, when a caulking load generated by the caulking portion 20a is applied to the proximal-end facing surface 30e of the metal ring 30 (to be more specific, the proximal-end facing surface 30j of the outer peripheral portion 30a), the center axis 30Ce is positioned more outside in the radial direction than a fulcrum on a proximal-end facing surface 10Bd of the proximal end portion 10B of the insulation member 10 which supports such a caulking load (the center axis 10Ce of the insulation member 10 in the radial direction). Accordingly, in terms of moment, on the proximal-end facing surface 30e of the metal ring 30, a large portion of a load $P_1$ generated by the caulking portion 20a is applied to a portion of the metal ring 30 outside the center axis 30Ce in the radial direction.

To the contrary, on a distal-end facing surface 30d of the metal ring 30, a major portion of a repulsive force $P_2$ from the insulation member 10 side is applied to a portion of the metal ring 30 more inside in the radial direction than the center axis 30Ce.

Accordingly, to consider the metal ring 30 as a whole, a stress (bending moment) $S_1$ which presses the outer peripheral portion 30a of the metal ring 30 downward (toward a distal end) is applied to the metal ring 30. Here, the stress $S_1$ is generated due to the positional relationship with the fulcrum of the above-mentioned insulation member 10 so long as the outer peripheral portion 30a (outer surface 30f) of the metal ring 30 projects outward in the radial direction from the outer surface 10Bf of the proximal end portion 10B of the insulation member 10, and at least the inner surface 30i of the metal ring 30 is coplanar with the inner surface 10i of the insulation member 10 or the inner surface 30i is positioned outside the inner surface 10i. However, as described later, when the inner surface 30i is positioned outside the inner surface 10i, the stress $S_1$ is further increased and hence, such positional relationship is preferable.

The caulking portion 20a is brought into close contact with the whole proximal-end facing surface 30j of the outer peripheral portion 30a of the metal ring 30 and hence, the load $P_1$ generated by the caulking portion 20a is surely applied to the outer peripheral portion 30a whereby the stress $S_1$ is further increased.

In addition, a gap G is defined between a portion of the proximal-end facing surface 30h of the inner peripheral portion 30b of the metal ring 30 which is arranged more inside in the radial direction than a position (facing region R) where the metal ring 30 faces the inner end 20ap of the caulking portion 20a in an opposed manner and the caulking portion 20a and hence, the inner end 20ap and a portion of the inner peripheral portion 30b are spaced apart from each other. Accordingly, a position of the caulking portion 20a where the caulking portion 20a is brought into contact with the proximal-end facing surface 30e of the metal ring 30 and a caulking load is applied to the metal ring 30 is positioned on an outer peripheral portion 30a side of the metal ring 30. Due to such a constitution, the stress $S_1$ explained in conjunction with FIG. 3A and FIG. 3B which presses the outer peripheral portion 30a side of the metal ring 30 downward (toward a distal end) is easily applied to the metal ring 30 and hence, the above-mentioned spring back effect can be surely acquired.

Figure 3B:
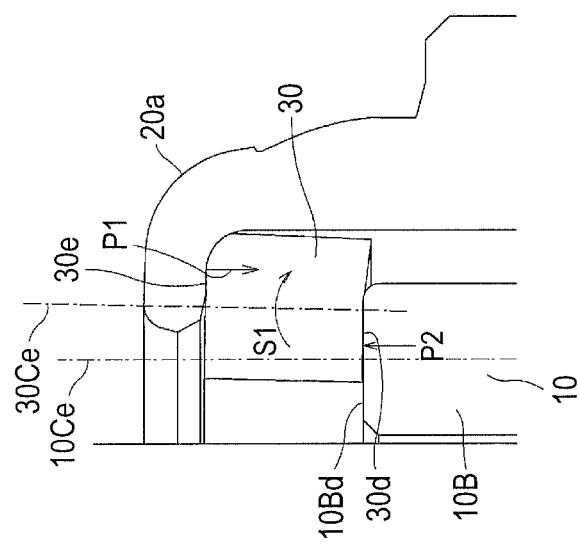

On the other hand, as shown in FIG. 3B, when the gas sensor 100 is heated, the caulking portion 20a made of metal is more elongated in the longitudinal direction (in the ex direction in FIG. 3B) than the insulation member 10 made of ceramic or the like. Here, the metal ring 30 springs back in the direction $S_2$ opposite to the direction that the stress $S_1$ is applied (that is, in the direction that the outer peripheral portion 30a of the metal ring 30 returns upward (toward a proximal end)). Further, due to this spring-back, the distal-end facing surface 30d of the metal ring 30 presses the insulation member 10 downward toward a distal end (indicated by an arrow Px) and hence, the loosening of caulking can be prevented whereby the deterioration of gas tightness obtained by the sealing material 6 can be suppressed.

When the outer peripheral portion 30a (outer surface 30f) of the metal ring 30 excessively projects outward from the outer surface 10Bf of the proximal end portion 10B of the insulation member 10 or when a thickness of the metal ring 30 is excessively small, there exists a possibility that the metal ring 30 exceeds an elastic limit thereof and is plastically deformed at the time of caulking so that the above-mentioned spring back effect cannot be acquired. Accordingly, it is preferable to adjust these factors such that the metal ring 30 does not exceed the elastic limit thereof by caulking. For example, the metal ring 30 may be formed using stainless steel (for example, SUS430).

As described above, even when the caulking portion 20a is expanded in the longitudinal direction by heat, a spring force of the metal ring 30 which is elastically deformed remains so that a force in the direction which pushes the insulation member 10 downward toward a distal end and tightens the sealing material (talc powder) 6 remains. Accordingly, the deterioration of the gas tightness at a high temperature can be suppressed, and the gas tightness can be held even after the thermal cycle.

Further, in FIG. 2, a distal-end facing surface 30d2 of the outer peripheral portion 30a of the metal ring 30 is positioned on a more distal end side than the proximal-end facing surface 10Bd of the proximal end portion 10B of the insulation member 10. Here, the distal-end facing surface 30d2 of the metal ring 30 is a surface positioned in the vicinity of the outer peripheral portion 30a of the metal ring 30 and projects downward (toward a distal end side) from the distal-end facing surface 30d which is a portion of the metal ring 30 brought into contact with the insulation member 10. That is, the metal ring 30 forcibly enters a gap A defined between the insulation member 10 and the housing 20 and hence, the distal-end facing surface 30d and the distal-end facing surface 30d2 are not made coplanar with each other. To differentiate both the distal-end facing surface 30d and the distal-end facing surface 30d2 from each other, symbols 30d, 30d2 are respectively given.

In this manner, a major portion of a caulking load is applied to an outer side of the metal ring 30 to an extent that the distal-end facing surface 30d of the metal ring 30 is bent downward more than an imaginary line L which indicates an extending line extended from the proximal-end facing surface 10Bd of the insulation member 10 (the imaginary line L passing the distal-end facing surface 30d). Accordingly, as shown in FIG. 3, the stress $S_1$ which presses the outer peripheral portion 30a of the metal ring 30 downward (toward the distal end) is increased. Further, the above-mentioned spring back effect is also increased along with the increase of the stress $S_1$ and hence, the loosening of caulking can be prevented in the same manner as described above whereby the deterioration of gas tightness obtained by the sealing material 6 can be suppressed.

Further, as shown in FIG. 3B, it is preferable that a contact portion 30g between the caulking portion 20a and the metal ring 30 is positioned more inside in the radial direction than the outer surface 10Bf of the insulation member 10 (that is, the proximal-end facing surface 30h of the inner peripheral portion 30b of the metal ring 30). Due to such a constitution, it is possible to prevent a phenomenon that only the outer peripheral portion 30a of the metal ring 30 is deformed while applying a caulking load to the outer peripheral portion 30a side of the metal ring 30 and hence, it is possible to acquire a sufficient spring back effect.

Further, it is preferable that a cross section of the metal ring 30 taken along a plane in the axial direction of the gas sensor 100 has a rectangular shape. In this case, the distal-end facing surface 30d and the proximal-end facing surface 30e of the metal ring 30 become a planar surface respectively so that an area where the metal ring 30 is brought into contact with the caulking portion 20a and an area where the metal ring 30 is brought into contact with the proximal-end facing surface 10Bd of the proximal end portion 10B of the insulation member 10 are increased respectively. Accordingly, a spring force generated by the above-mentioned spring back can be surely applied to these members. The metal ring 30 having a rectangular cross section can be manufactured by blanking a flat plate, for example. By forming the distal-end facing surface 30d of the metal ring into a shape which allows the distal-end facing surface 30d to be in face contact with the proximal-end facing surface 10Bd of the insulation member 10, at least a spring force generated by the spring back can be further surely applied to these members.

Further, it is preferable that the inner end 20ap of the caulking portion 20a is positioned more outside in the radial direction than the inner surface 30i of the metal ring 30. Due to such a constitution, a position where a caulking load is applied to the metal ring 30 is arranged closer to an outer peripheral side than an inner peripheral side of the metal ring 30. Accordingly, a stress which presses the outer peripheral side of the metal ring 30 downward (toward a distal end) can be easily applied to the metal ring 30 and hence, the above-mentioned spring back effect can be easily acquired correspondingly.

Figure 4:
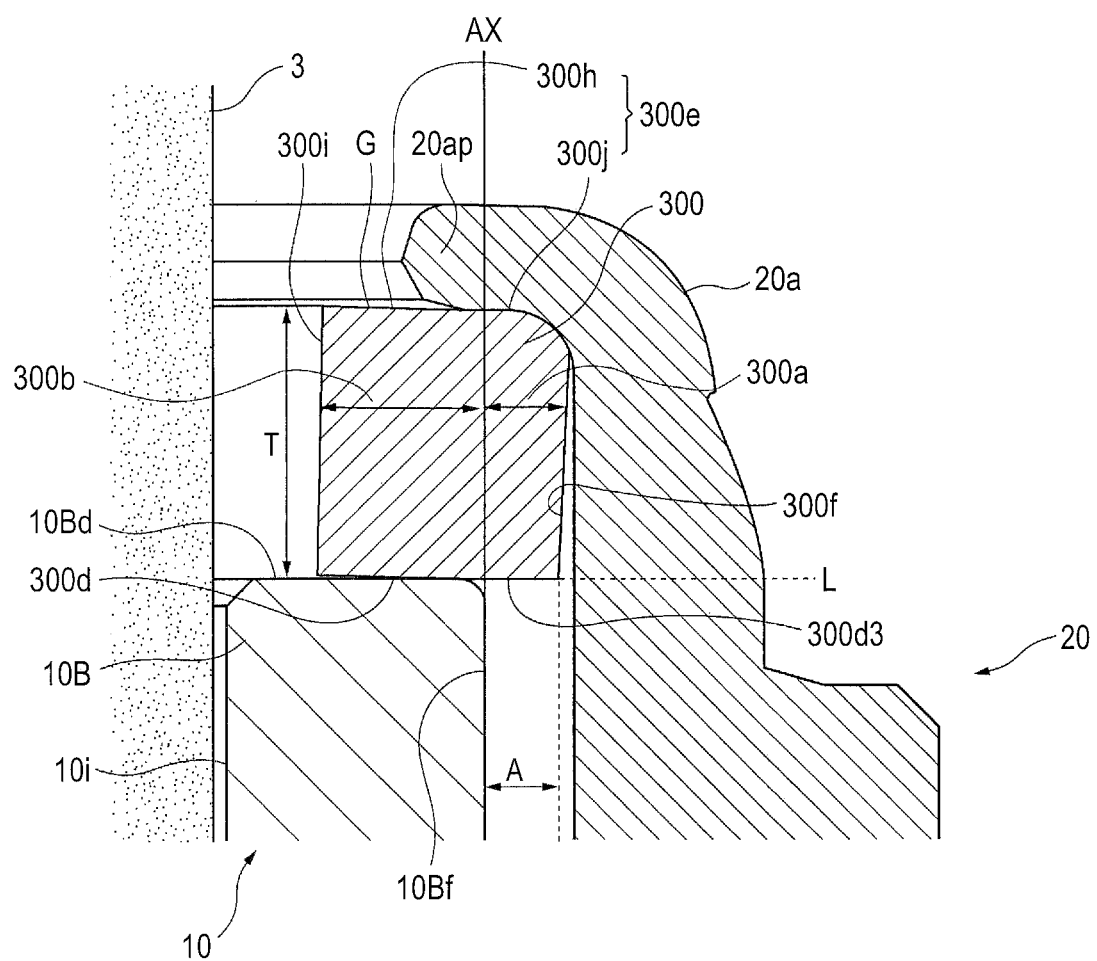
FIG. 4 is a cross-sectional view showing the positional relationship among the metal ring, an insulation member, and a housing of a gas sensor according to a second embodiment of the present invention.

Next, a gas sensor according to a second embodiment of the present invention is explained in conjunction with FIG. 4. Here, the gas sensor according to the second embodiment has the substantially same constitution as the first embodiment except for a shape of a metal ring 300. Accordingly, in FIG. 4, the positional relationship among the metal ring 300, an insulation member 10 and a housing 20 corresponding to the positional relationship shown in FIG. 2 is shown as a cross-sectional view, while the explanation of other constitutions of gas sensor of the second embodiment is omitted.

In FIG. 4, a distal-end facing surface 300d3 of the metal ring 300 is arranged parallel to an imaginary line L or is arranged above the imaginary line L and hence, the metal ring 300 does not forcibly enter a gap defined between the insulation member 10 and the housing 20, and distal-end facing surfaces 300d, 300d3 are made coplanar with each other.

Also in such a gas sensor, an outer diameter of the metal ring 300 is set larger than an outer diameter of the insulation member 10 and hence, an outer peripheral portion 300a of the metal ring 300 projects outward in the radial direction from an outer surface 10Bf of a proximal end portion 10B of the insulation member 10. Further, a caulking portion 20a is brought into close contact with a whole proximal-end facing surface 300j of an outer peripheral portion 300a of the metal ring 300. Further, an inner end 20ap of the caulking portion 20 is partially spaced apart from a proximal-end facing surface 300h of the inner peripheral portion 300b of the metal ring 300 (radially inner end portion of the proximal-end facing surface 300h).

In this embodiment, an inner end 20ap of the caulking portion 20a is positioned more outside in the radial direction than an inner surface 300i of the metal ring 300. Further, in this embodiment, the inner surface 300i of the metal ring 300 is positioned more outside in the radial direction than an inner surface 10i of the insulation member 10. However, it is not a requisite to position the inner surface 300i more outside in the radial direction than the inner surface 10i, and the inner surface 300i may be made coplanar with the inner surface 10i. Here, in view of the relationship which allows the insertion of the sensor element 3, there is no case where the inner surface 300i is positioned more inside in the radial direction than the inner surface 10i.

As described above, the outer peripheral portion 300a of the metal ring 300 projects outward in the radial direction from the outer surface 10Bf of the proximal end portion 10B of the insulation member 10 and hence, as shown in FIG. 3A showing the first embodiment, a center axis 300Ce of the metal ring 300 is offset outward in the radial direction from a center axis 10Ce of the insulation member 10 in the radial direction. That is, when a caulking load generated by the caulking portion 20a is applied to the proximal-end facing surface 300e of the metal ring 300 (the outer peripheral portion 300a), the center axis 30Ce is positioned more outside in the radial direction than a fulcrum on a proximal-end facing surface 10Bd of the proximal end portion 10B of the insulation member 10 which supports such a caulking load (the center axis 10Ce of the insulation member 10 in the radial direction). Accordingly, in terms of moment, on the proximal-end facing surface 300e of the metal ring 300, a large portion of a load $P_1$ generated by the caulking portion 20a is applied to a portion of the metal ring 300 outside the center axis 300Ce in the radial direction.

To the contrary, on a distal-end facing surface 300d of the metal ring 300, a major portion of a repulsive force $P_2$ from the insulation member 10 side is applied to a portion of the metal ring 300 more inside in the radial direction than the center axis 300Ce.

Accordingly, to consider the metal ring 300 as a whole, a stress (bending moment) $S_1$ which presses the outer peripheral portion 300a of the metal ring 300 downward (toward a distal end) is applied to the metal ring 300. Here, the stress $S_1$ is generated due to the positional relationship with the fulcrum of the above-mentioned insulation member 10 so long as the outer peripheral portion 300a (outer surface 300f) of the metal ring 300 projects outward in the radial direction from the outer surface 10Bf of the proximal end portion 10B of the insulation member 10, and at least the inner surface 300i of the metal ring 300 is coplanar with the inner surface 10i of the insulation member 10 or the inner surface 300i is positioned outside the inner surface 10i. However, as described later, when the inner surface 300i is positioned outside the inner surface 10i, the stress $S_1$ is further increased and hence, such positional relationship is preferable.

The caulking portion 20a is brought into close contact with the whole proximal-end facing surface 300j of the outer peripheral portion 300a of the metal ring 300 and hence, the load P1 generated by the caulking portion 20a is surely applied to the outer peripheral portion 300a whereby the stress S1 is further increased.

In addition, a gap G is defined between a portion of the proximal-end facing surface 300h of the inner peripheral portion 300b of the metal ring 300 which is arranged more outside in the radial direction than a position where the metal ring 300 faces the inner end 20ap of the caulking portion 20a in an opposed manner and the caulking portion 20a and hence, the inner end 20ap and a portion of the inner peripheral portion 300b are spaced apart from each other. Accordingly, a position of the caulking portion 20a where the caulking portion 20a is brought into contact with the proximal-end facing surface 300e of the metal ring 300 and a caulking load is applied to the metal ring 300 is positioned on an outer peripheral portion 300a side of the metal ring 300. Due to such a constitution, the stress $S_1$ explained in conjunction with FIG. 3 which presses the outer peripheral portion 300a side of the metal ring 300 downward (toward a distal end) is easily applied to the metal ring 300 and hence, the above-mentioned spring back effect can be surely acquired.

On the other hand, as shown in FIG. 3B which shows the first embodiment, when the gas sensor 100 is heated, the caulking portion 20a made of metal is more elongated in the longitudinal direction (in the ex direction in FIG. 3) than the insulation member 10 made of ceramic or the like. Here, the metal ring 300 springs back in the direction $S_2$ opposite to the direction that the stress $S_1$ is applied (that is, in the direction that the outer peripheral portion 300a of the metal ring 300 returns upward (toward a proximal end)). Further, due to this spring-back, the distal-end facing surface 300d of the metal ring 300 presses the insulation member 10 downward toward a distal end (indicated by an arrow Px) and hence, the loosening of caulking can be prevented whereby the deterioration of gas tightness obtained by the sealing material 6 can be suppressed.

As described above, even when the caulking portion 20a is expanded in the longitudinal direction by heat, a spring force of the metal ring 300 which is elastically deformed remains so that a force which pushes the insulation member 10 downward toward a distal end and tightens the sealing material (talc powder) 6 remains. Accordingly, the deterioration of the gas tightness at a high temperature can be suppressed, and the gas tightness can be held even after the thermal cycle.

Further, also in the second embodiment, it is preferable that a contact portion between the caulking portion 20a and the metal ring 300 is positioned more inside in the radial direction than the outer surface 10Bf of the insulation member 10 (that is, the proximal-end facing surface 300h of the inner peripheral portion 300b of the metal ring 300). Due to such a constitution, it is possible to prevent phenomenon that only the outer peripheral portion 300a of the metal ring 300 is deformed while applying a caulking load to the outer peripheral portion 300a side of the metal ring 300 and hence, it is possible to acquire a sufficient spring back effect.

In the first and second embodiments, the inner surface 30i, 300i of the metal ring 30, 300 is positioned more outside in the radial direction than the inner surface 10i of the insulation member 10. An advantageous effect acquired by such a constitution is explained in conjunction with FIG. 5A and FIG. 5B by taking a metal ring 31 which has an inner surface 31i thereof made coplanar with the inner surface 10i of the insulation member 10 as an example.

Figure 5:
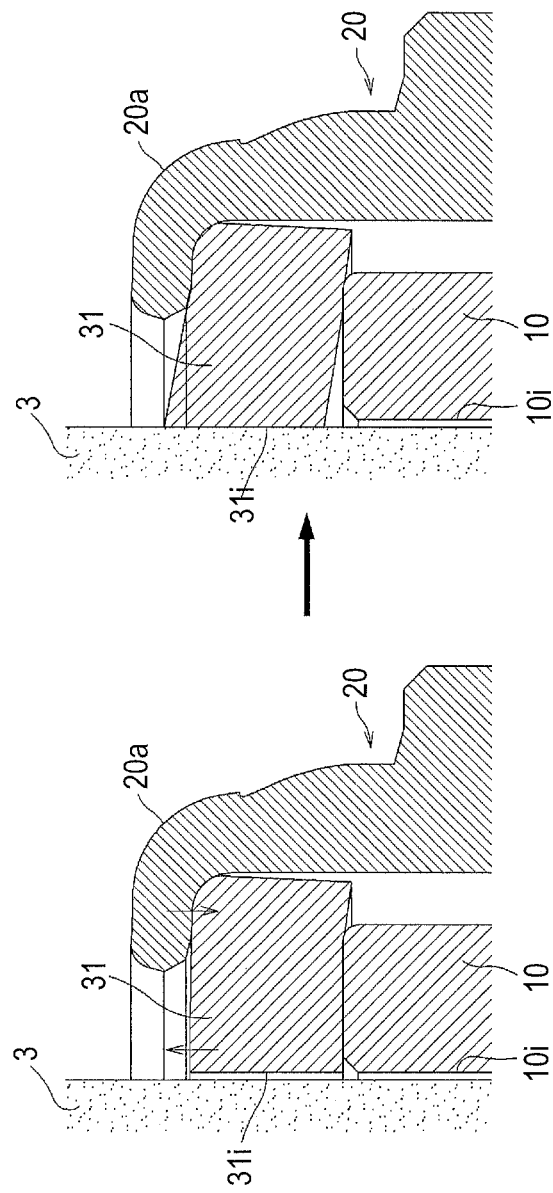
FIG. 5A and FIG. 5B are views showing the manner of operation of the gas sensor when an inner surface of the metal ring is positioned more outside in the radial direction than an inner surface of the insulation member.

Firstly, when the caulking is made while applying a major portion of a caulking load to an outer peripheral side of the metal ring 31 by the caulking portion 20a (FIG. 5A), the outer peripheral side of the metal ring 31 is pressed downward, and along with such downward pressing, an inner peripheral side of the metal ring 31 is pressed upward (toward a proximal end side) (FIG. 5B). When the inner surface 31i of the metal ring 31 is made coplanar with the inner surface 10i of the insulation member 10, there may be a case where, when the inner peripheral portion side of the metal ring 31 is pressed upward, the inner surface 31i is caught by an outer surface of the sensor element 3 or the like and hence, the caulking operation becomes difficult.

Accordingly, as shown in FIG. 2 and FIG. 4, by positioning the inner surface 30i of the metal ring 30 more outside in the radial direction than the inner surface 10i of the insulation member 10, the above-mentioned catch is decreased and hence, the caulking can be surely performed.

Figure 6:
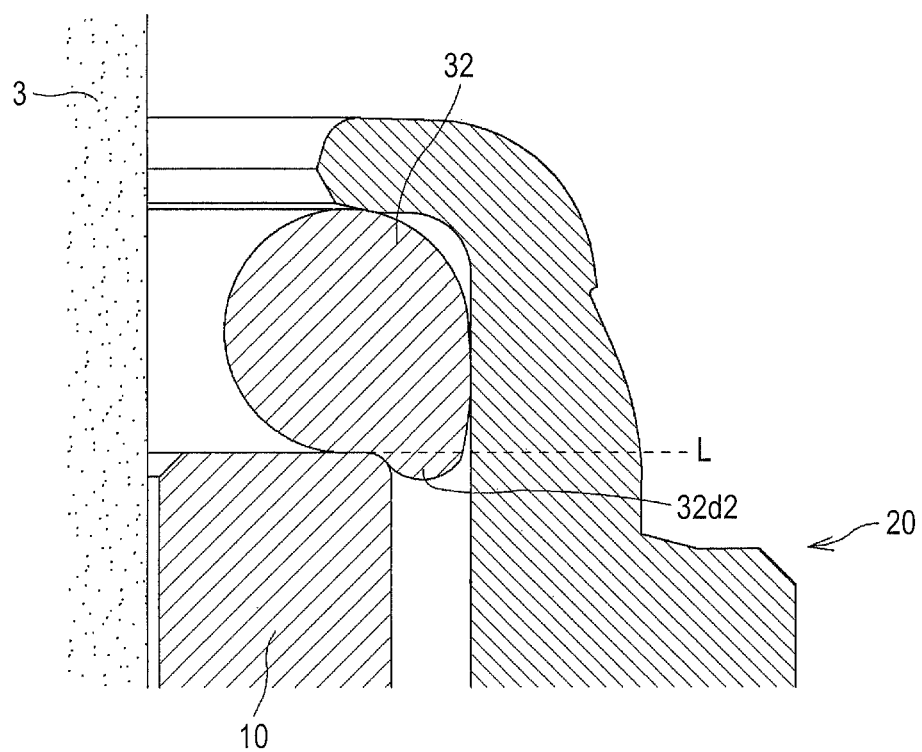
FIG. 6 is a view showing an example where a shape of a cross section of the metal ring is not a rectangular shape.

Here, as shown in FIG. 6, a cross section of a metal ring 32 taken along a plane in the axial direction of the gas sensor 100 may have a shape different from a rectangular shape (a circular cylindrical shape in an example shown in FIG. 6). As such a metal ring 32, a metal hollow ring having a circular shape, an elliptical shape or a tubular shape can be named. It is needless to say that a solid ring may be used.

The metal ring 32 may also preferably be configured such that a distal-end facing surface 32d2 of an outer peripheral portion 32a is positioned below an imaginary line L (toward a distal end side). However, in the case of the metal ring 32, a surface of the metal ring 32 is not a planar surface and hence, it is not always the case that an outermost periphery of the metal ring 32 projects downward toward a distal end side, and there may be a case where a portion of the metal ring 32 which is slightly inside an outer periphery is positioned below the imaginary line L. Accordingly, it is sufficient that an outer peripheral portion of the metal ring 32 which projects outward in the radial direction from the proximal end portion 10B of the insulation member 10 is positioned below the imaginary line (toward a distal end side).

Figure 7:
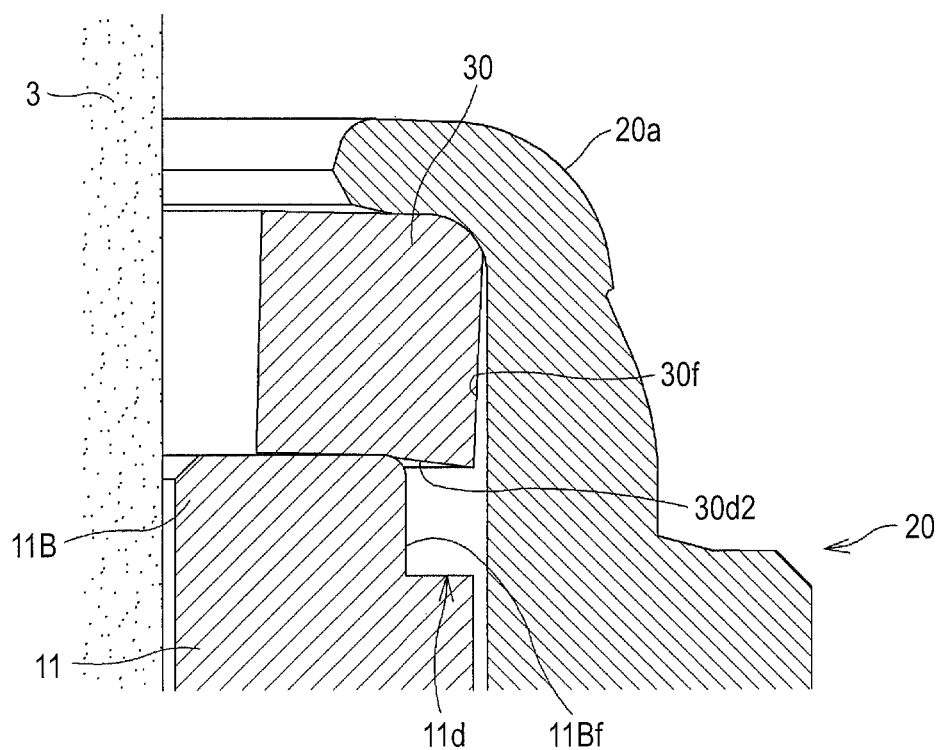
FIG. 7 is a view showing an example in which a proximal end portion of the insulation member has a diameter smaller than a diameter of other portions of the insulation member.

Further, as shown in FIG. 7, a stepped portion 11d may be formed by narrowing an outer surface 11Bf of a proximal end portion 11B of an insulation member 11 than a diameter of an outer surface of a remaining portion of the insulation member 11. That is, it is sufficient that at least an outer surface 30f of the metal ring 30 projects outward at a proximal end portion 11B of the insulation member 11, and it is unnecessary for the metal ring 30 to project outward at a remaining portion of the insulation member 11. Here, it is preferable that the outer surface 11Bf of the insulation member 11 is formed into a straight shape since cracks do not occur in the insulation member 10.

Further, in the first and second embodiments, the inner end 20ap of the caulking portion 20a is positioned more outside in the radial direction than the inner surface 30i, 300i of the metal ring 30, 300. However, the present invention is not limited to the above-mentioned embodiments and, as shown in FIG. 8, an inner end 21ap of a caulking portion 21a may be positioned more inside in the radial direction than the inner surface 30i of the metal ring 30. Also in this case, the caulking portion 21a is brought into close contact with a whole proximal-end facing surface 30j of an outer peripheral portion 30a of the metal ring 30, and with respect to the proximal-end facing surface 30h of the inner peripheral portion 30b of the metal ring 30, a gap G is defined between a radially inner end portion 30t and the caulking portion 21a and hence, the caulking portion 21a and a portion of the inner peripheral portion 30b are spaced apart from each other. Accordingly, a position where the caulking portion 21a is brought into contact with the proximal-end facing surface 30e of the metal ring 30 and a caulking load is applied to the metal ring 30 is arranged on an outer peripheral portion 30*a* side of the metal ring 30 and hence, the above-mentioned spring back effect can be surely acquired.

In the first embodiment, the inner end 20*ap* and the portion of the inner peripheral portion 30*b* are spaced apart from each other. However, the present invention is not limited to the above-mentioned constitution, and the inner end 20*ap* and the inner peripheral portion 30*b* may be brought into close contact with each other provided that the distal-end facing surface 30*d*2 of the outer peripheral portion 30*a* of the metal ring 30 is positioned on a more distal end side than the proximal-end facing surface 10Bd of the proximal end portion 10B of the insulation member 10 (that is, the metal ring 30 forcibly enters a gap defined between the insulation member 10 and the housing 20).

It is needless to say that the present invention is not limited to the above-mentioned embodiments, and the present invention covers various modifications and equivalents which are included in the technical concept and the scope of the present invention.

EXAMPLE

As a simulation, a magnitude of spring back (repulsive force) is experimentally studied by changing the distance A (see FIG. 2) in the radial direction between the outer surface 30*f* of the outer peripheral portion of the metal ring 30 and the outer surface 10Bf of the proximal end portion 10B of the insulation member 10. In the simulation, the caulking-portion structure of the gas sensor shown in FIG. 2 is used, and materials (to be more specific, thermal expansion coefficients, Young's moduli and the like) and positions of the respective constitutional parts are set. A thickness T of the metal ring 30 is set to 2.0 mm, and SUS430 is used as a material of the metal ring 30.

Then, the caulking portion 20*a* is pressed downward by 0.4 mm toward a distal end side at a normal temperature (20° C.) and, thereafter, the load is removed. A repulsive force which is generated due to a change in position of the respective constitutional parts in the above caulking operation is analyzed as a bearing pressure applied to a distal-end facing surface (an interface between the insulation member 10 and the sealing material 6) of the insulation member 10 from a sealing material 6 side. The repulsive force (bearing pressure) can be calculated based on a force which attempts to return the constitutional parts to original positions corresponding to Young's moduli when positions of the respective constitutional parts are displaced.

Figure 9:
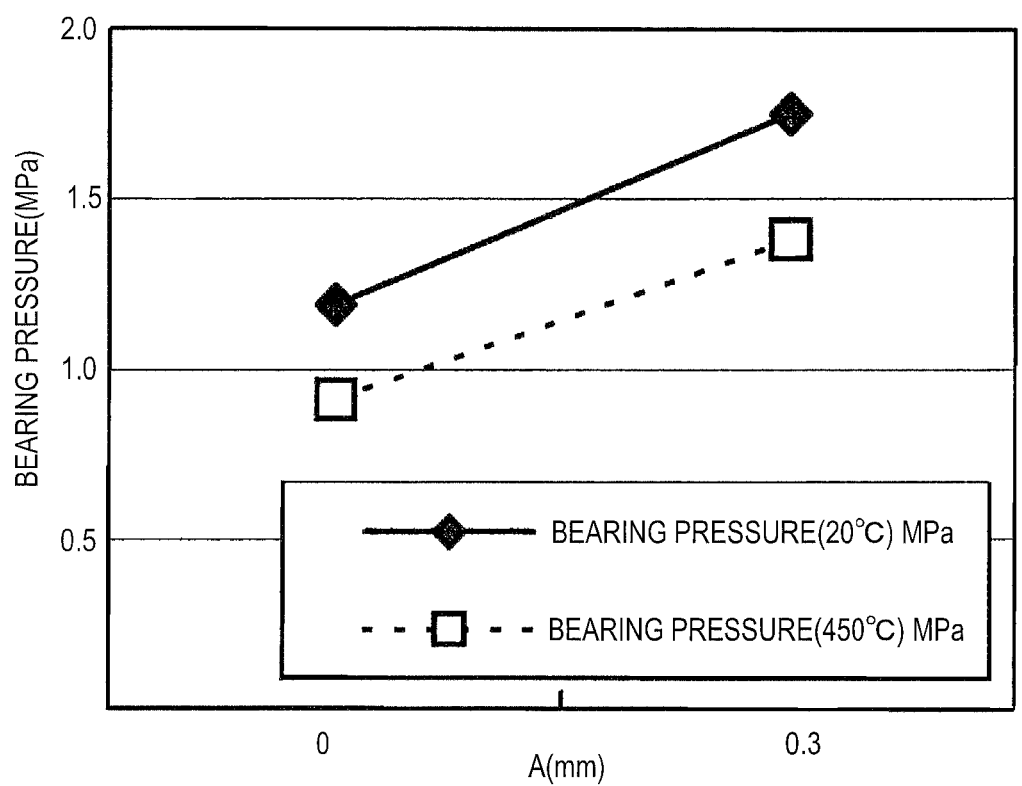
FIG. 9 is a view showing a magnitude of a bearing pressure by simulation when a distance in the radial direction between an outer surface of an outer peripheral portion of the metal ring and an outer surface of a proximal end portion of the insulation member is changed.
Figure 10:
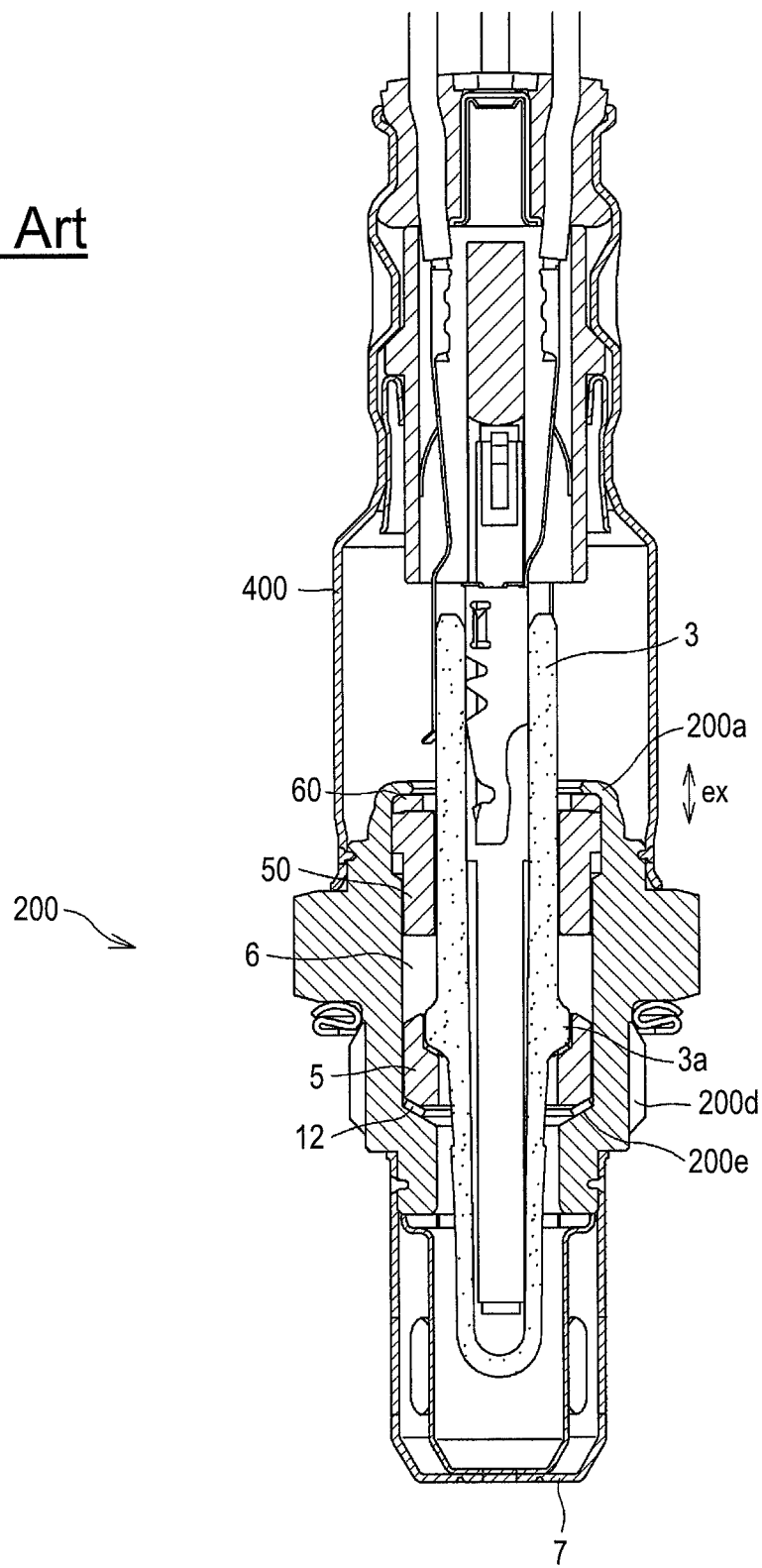
FIG. 10 is a view showing the structure around a caulking portion of a conventional gas sensor.

Next, the gas sensor 100 is heated to 450° C., and the change in position of the respective constitutional parts which is brought about by elongation caused by the thermal expansion of the respective constitutional parts is calculated. Further, the above-mentioned bearing pressure at a temperature of 450° C. is analyzed based on Young's modules of the respective constitutional parts corresponding to such change in position. A result of the analysis carried out by changing the distance A to 0 mm and 0.3 mm is shown in FIG. 9. Here, under the condition where the distance A is set to 0.3 mm, as shown in FIG. 2, the inner end 20*ap* of the caulking portion 20*a* is spaced apart from the metal ring 30.

As can be clearly understood from FIG. 9, it is understood that by projecting the outer surface 30*f* of the outer peripheral portion of the metal ring 30 outward from the outer surface 10Bf of the proximal end portion 10B of the insulation member 10, the bearing pressure is elevated so that the spring back is increased.

What is claimed is:

1. A gas sensor comprising:
a cylindrical housing which extends in a longitudinal direction of the gas sensor;
a sensor element inserted into the inside of the housing while having a distal end side thereof projecting from a distal end of the housing;
a sealing material which is filled in a gap between the sensor element and the housing;
a cylindrical insulation member which is arranged on a proximal end side of the sealing material so as to surround the sensor element and having at least an outer surface of the proximal end portion thereof spaced apart from an inner surface of the housing; and
an annular metal ring which is arranged on a proximal end side of the insulation member and has an outer peripheral portion thereof projecting outward in a radial direction from the proximal end portion of the insulation member, wherein
the sealing material, the insulation member and the metal ring are fixed by caulking in a pressed state from a proximal end side to a distal end side by a caulking portion which is formed by bending a proximal end portion of the housing inward,
the caulking portion is brought into close contact with a whole proximal-end facing surface of the outer peripheral portion of the metal ring, and
a portion of an inner end of the caulking portion is gradually spaced apart in the longitudinal direction from a radially inner end portion of a proximal-end facing surface of the metal ring at an opposing region where the caulking portion and the metal ring face each other in an opposed manner in the longitudinal direction.

2. A gas sensor according to claim 1, wherein an inner end of the caulking portion is positioned on a more outside area in the radial direction than the inner surface of the metal ring.

3. A gas sensor according to claim 1, wherein a contact portion between the caulking portion and the metal ring is positioned more inside in the radial direction than an outer surface of the insulation member.

4. A gas sensor according to claim 1, wherein the inner surface of the metal ring is positioned more outside in the radial direction than the inner surface of the insulation member.

5. A gas sensor according to claim 1, wherein a distal-end facing surface of the metal ring is brought into face contact with the insulation member.

6. A gas sensor according to claim 5, wherein a cross section of the metal ring cut along a plane extending in the longitudinal direction has a rectangular shape.

7. A gas sensor according to claim 1, wherein an outer surface of the insulation member is formed into a straight shape.

8. A gas sensor comprising:
a cylindrical housing which extends in a longitudinal direction of the gas sensor;
a sensor element inserted into the inside of the housing while having a distal end side thereof projecting from a distal end of the housing;
a sealing material which is filled in a gap between the sensor element and the housing;
a cylindrical insulation member which is arranged on a proximal end side of the sealing material so as to surround the sensor element and having at least an outer surface of the proximal end portion thereof spaced apart from an inner surface of the housing; and an annular metal ring which is arranged on a proximal end side of the insulation member and has an outer peripheral portion thereof projecting outward in a radial direction from the proximal end portion of the insulation member, wherein the sealing material, the insulation member and the metal ring are fixed by caulking in a pressed state from a proximal end side to a distal end side by a caulking portion which is formed by bending a proximal end portion of the housing inward, and a distal-end facing surface of the outer peripheral portion of the metal ring is positioned downward more than an imaginary line extending from a proximal-end facing surface of the insulation member.

9. A gas sensor according to claim 8, wherein the caulking portion is brought into close contact with the whole proximal-end facing surface of the outer peripheral portion of the metal ring, and at the inner peripheral portion of the metal ring formed inside the outer peripheral portion, at least a radially inner end portion of the proximal-end facing surface of the metal ring in an opposing region where the caulking portion and the metal ring face each other in an opposed manner in the longitudinal direction is spaced apart from the caulking portion.

* * * * *